(12) United States Patent
Peterson et al.

(10) Patent No.: US 11,547,423 B2
(45) Date of Patent: Jan. 10, 2023

(54) MEDICAL TOURNIQUET

(71) Applicant: Acme United Corporation, Fairfield, CT (US)

(72) Inventors: Alan Peterson, Trumbull, CT (US); David Budd, Newtown, CT (US)

(73) Assignee: Acme United Corporation, Fairfield, CT (US)

( * ) Notice: Subject to any disclaimer, the term of this patent is extended or adjusted under 35 U.S.C. 154(b) by 178 days.

(21) Appl. No.: 17/102,994

(22) Filed: Nov. 24, 2020

(65) Prior Publication Data
US 2021/0153873 A1    May 27, 2021

Related U.S. Application Data

(60) Provisional application No. 62/940,468, filed on Nov. 26, 2019.

(51) Int. Cl.
*A61B 17/132* (2006.01)
(52) U.S. Cl.
CPC .............................. *A61B 17/1322* (2013.01)
(58) Field of Classification Search
CPC .............. A61B 17/132; A61B 17/1322; A61B 17/1325; A61B 17/1327
See application file for complete search history.

(56) References Cited

U.S. PATENT DOCUMENTS

| | | | |
|---|---|---|---|
| 6,884,254 B2 | 4/2005 | Brooks | |
| 6,899,720 B1 | 5/2005 | McMillan | |
| 7,776,064 B2 | 8/2010 | Johnson et al. | |
| 7,842,067 B2 | 11/2010 | Esposito | |
| 7,892,253 B2 | 2/2011 | Esposito et al. | |
| D649,642 S | 11/2011 | Johnson | |
| 8,047,850 B2 | 11/2011 | Esposito et al. | |
| 8,303,620 B2 | 11/2012 | Johnson et al. | |
| 8,343,182 B2 | 1/2013 | Kirkham | |
| 8,348,970 B2 | 1/2013 | Janota | |
| 8,888,807 B2 | 11/2014 | Esposito | |
| D739,027 S | 9/2015 | Johnson et al. | |
| 9,730,703 B2 * | 8/2017 | Rose | A61B 17/1322 |
| D810,300 S * | 2/2018 | Parsons | D24/169 |
| 10,016,203 B2 | 7/2018 | Esposito | |
| 10,085,900 B2 | 10/2018 | Johnson et al. | |
| 10,194,917 B1 | 2/2019 | Carson et al. | |
| 10,249,218 B2 * | 4/2019 | Bronson | G09B 23/28 |
| 10,258,347 B2 | 4/2019 | Hopman et al. | |
| 10,321,917 B2 | 6/2019 | Ugh et al. | |
| 10,335,160 B1 | 7/2019 | Holloman et al. | |

(Continued)

*Primary Examiner* — Ryan J. Severson
(74) *Attorney, Agent, or Firm* — Alix, Yale & Ristas, LLP

(57) ABSTRACT

A compression assembly for a medical tourniquet comprises a strap, a windlass and a buckle assembly and employs a retainer which retains the windlass upon rotation to apply pressure to a limb. The retainer has a pair of C-shaped portions which retain the windlass and a cross piece which is captured by a mounting strip. The buckle assembly preferably comprises a pair of parallel bars, one of which mounts a clasp which engageably retains a D-shaped ring. The strap is pulled through the D-shaped ring and secured in a taut engagement about a limb. The tourniquet is cooperatively configured so that only a relatively small additional rotation of the windlass is typically required to apply the final occluding pressure.

20 Claims, 9 Drawing Sheets

(56) References Cited

U.S. PATENT DOCUMENTS

| | | | |
|---|---|---|---|
| 10,363,046 B2 | 7/2019 | Hopman et al. | |
| D858,774 S | 9/2019 | Parsons | |
| 10,398,447 B2 | 9/2019 | Keinan et al. | |
| 10,492,796 B2 | 12/2019 | Bennett | |
| D906,168 S * | 12/2020 | Parsons | D11/218 |
| 2005/0273134 A1* | 12/2005 | Esposito | A61B 17/1327 606/203 |
| 2009/0005804 A1 | 1/2009 | Esposito et al. | |
| 2009/0062842 A1* | 3/2009 | Esposito | A61B 17/1327 606/203 |
| 2010/0057120 A1* | 3/2010 | Kirkham | A61B 17/1322 606/203 |
| 2011/0307004 A1* | 12/2011 | Johnson | A61B 17/1322 606/203 |
| 2012/0071917 A1* | 3/2012 | McDonald | G01L 5/102 116/212 |
| 2013/0267994 A1 | 10/2013 | Crowder et al. | |
| 2014/0277103 A1 | 9/2014 | Esposito | |
| 2015/0216536 A1* | 8/2015 | Hopman | A61B 17/135 606/202 |
| 2015/0257767 A1* | 9/2015 | Henderson | A61B 17/1327 441/75 |
| 2016/0345981 A1* | 12/2016 | Demas | A61B 17/1327 |
| 2016/0367262 A1* | 12/2016 | Burke | A61B 17/1322 |
| 2018/0168663 A1* | 6/2018 | Hill | A61B 17/1322 |
| 2018/0228497 A1* | 8/2018 | Dimino | A61F 15/006 |
| 2018/0317935 A1* | 11/2018 | Engwall | A61B 17/1327 |
| 2019/0223884 A1* | 7/2019 | Bennett | A61B 17/1327 |
| 2020/0015828 A1* | 1/2020 | Johnson | A44B 11/18 |
| 2020/0367909 A1* | 11/2020 | Rankins, III | A61B 17/1325 |
| 2021/0000482 A1* | 1/2021 | Parsons | A61B 17/1322 |
| 2021/0153873 A1* | 5/2021 | Peterson | A61B 17/1322 |
| 2021/0346035 A1* | 11/2021 | Wagner | A61B 17/1322 |
| 2022/0047273 A1* | 2/2022 | Parsons | A61B 17/1322 |

* cited by examiner

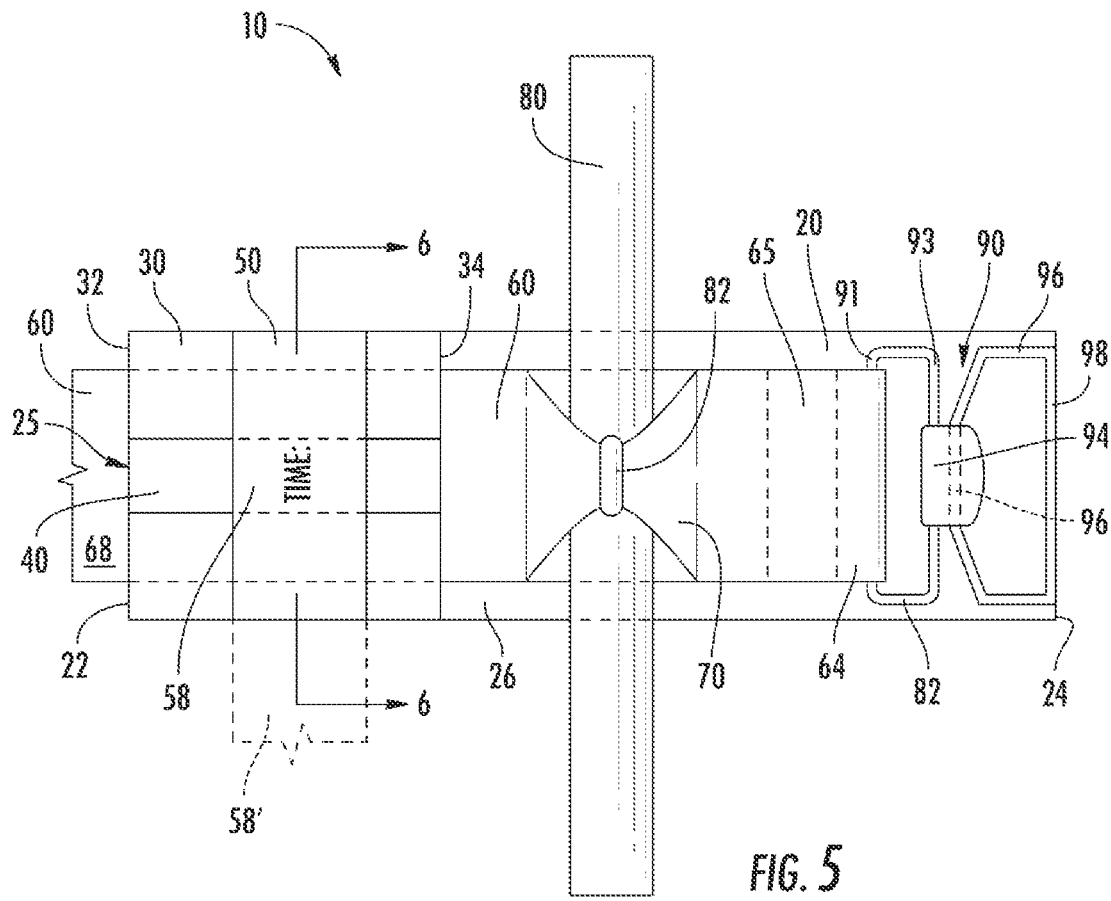
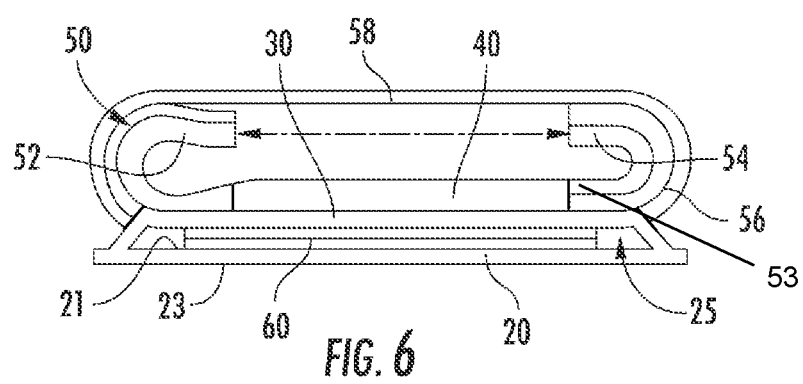

MEDICAL TOURNIQUET

CROSS-REFERENCE TO RELATED APPLICATION

This application claims the priority of U.S. Provisional Patent Application No. 62/940,468 filed on Nov. 26, 2019, which application is incorporated herein in its entirety.

BACKGROUND

This disclosure relates generally to tourniquets which are employed for medical emergencies. More particularly, this disclosure relates to tourniquets which are secured around a limb to constrict blood vessels and prevent excessive bleeding in emergency conditions.

Numerous tourniquet configurations and techniques have been advanced to address severe bleeding from the limbs. Such bleeding may potentially result in a catastrophic trauma requiring immediate intervention.

To be effective, a tourniquet must address a number of considerations. First, the tourniquet must be capable of readily terminating a bleeding condition while also not completely stopping the flow of blood to the extreme portions of a limb below the tourniquet away from the patient's heart. Second, the tourniquet must be readily adaptable for use in an efficient manner so that application of the tourniquet to the limb and the application of pressure between the heart and the wound is accomplished in an efficient reliable manner. Third, it is highly desirable that the tourniquet can be put into use by medical or paramedical personnel without extensive training and familiarity with the tourniquet. Fourth, the tourniquet should be configured so that once the threshold pressure is obtained to terminate the excessive bleeding from the wound, the pressure can be maintained for a sufficient time so that appropriate treatment can be rendered.

It is also important that the tourniquet be constructed from materials of high integrity and materials which are sufficiently compliant so that usage of the tourniquet does not result in excessive pain and discomfort. An additional beneficial feature is that the connecting and fastening components and the pressure applicators have sufficient structural and mechanical integrity so that the usage and maintenance of the tourniquet during the entire medical emergency situation is ensured.

SUMMARY

Briefly stated, a tourniquet in a preferred form comprises a first member and a second member having first and second ends attached at opposite sides to the first member to form a slide. A retainer having opposed catches is mounted to the second member. An elongated third member has opposed first and second sides and forms a closed first loop and a closed second loop. The third member is secured to the first member at a location between the first and second loops. A windlass has an eye which protrudes from a medial portion. The eye receives a portion of the third member extending to form the closed second loop. The windlass is capturable in the retainer. A clip has a pair of parallel bars. One bar is pivotally retained by the first loop. The second bar mounts a clasp. A D-ring is retained by the clasp. A hook and loop fabric connector is disposed on the first side of the third member. The third member is slidable in the slide between the first and second members and is engageable about a limb. The third member is insertable through the D-ring and is securable in a taut engagement by the hook and loop fabric connector. The third member is further tightenable by rotating the windlass to an occluding position which is maintainable by securing the windlass in the retainer.

The D-ring is dismountable from the clasp. The windlass has a quasi-rod-like shape with the eye protruding from a medial portion. The retainer comprises a plastic member having C-shaped catches. A strip of material secures the retainer to the second member. In one embodiment, the retainer comprises a pair of transversely spaced tabs which engage the strip of material.

The third member comprises two layers with elongated nylon material stitched longitudinally along opposed sides. A securement band is positionable over the catches and removably securable to the retainer. A reinforcement pad is attached to the first member. The tourniquet further comprises a cushion pad attached to the first member.

In another embodiment, a tourniquet comprises a first member and a second member having first and second ends attached at opposite sides to the first member. A retainer has opposed catches and a crosspiece with a pair of opposed tabs. A strip of material is mounted to the second member. The strip of material captures the crosspiece. An elongated third member has opposed first and second sides and forms closed first and second loops and is secured to the first member at a location between the loops. A windlass has an eye protruding from a medial portion which receives the third member extending to form the closed second loop. The windlass is capturable in the retainer. A first buckle member has a pair of parallel bars, one bar is pivotally retained by the first loop. The second bar mounts a clasp. A second buckle member is retainably engageable by the clasp. A hook and loop fabric connector is disposed on a first side of the third member. The third member is slidable between the first and second members and engageable about a limb. The third member also extends through the second buckle member and is securable in a taut engagement by the hook and loop fabric connector. The third member is also further tightenable by rotating the windlass to an occluding position maintainable by securing the windlass in the retainer.

The second buckle member is disengageable from the clasp. The retainer is preferably a plastic component.

In another embodiment, a connector is disposed on a first side of the third member. An enlarged pull member, preferably in the form of a D-ring, is mounted at an end of the third member. The third member is slidable between the first and second members and engageable about a limb. The third member extends through the second buckle member and is securable in a taut engagement by the connector. The third member is further tightenable by rotating the windlass to an occluding position which is maintainable by securing the windlass in the retainer.

The second buckle member is preferably a D-shaped ring. The retainer is preferably a plastic component and a securement band is mounted to the plastic component and is removably securable to the retainer.

BRIEF DESCRIPTION OF THE DRAWINGS

FIG. 5 is a top plan view of a portion of the tourniquet of FIG. 1, portions being shown in phantom;

FIG. 6 is a sectional view (partly exaggerated) of the tourniquet portion of FIG. 5 taken along the line 6-6 thereof;

DETAILED DESCRIPTION

With reference to the drawings wherein like numerals represent like parts throughout the figures, a tourniquet adapted for emergency trauma conditions is generally designated by the numeral 10. The tourniquet 10 functions to be easily applied to a limb to terminate excessive bleeding and to maintain sufficient pressure until proper medical treatment can be performed. The tourniquet 10 can be effectively employed without significant training and its proper usage is self-evident from the efficient construction.

Figure 1:
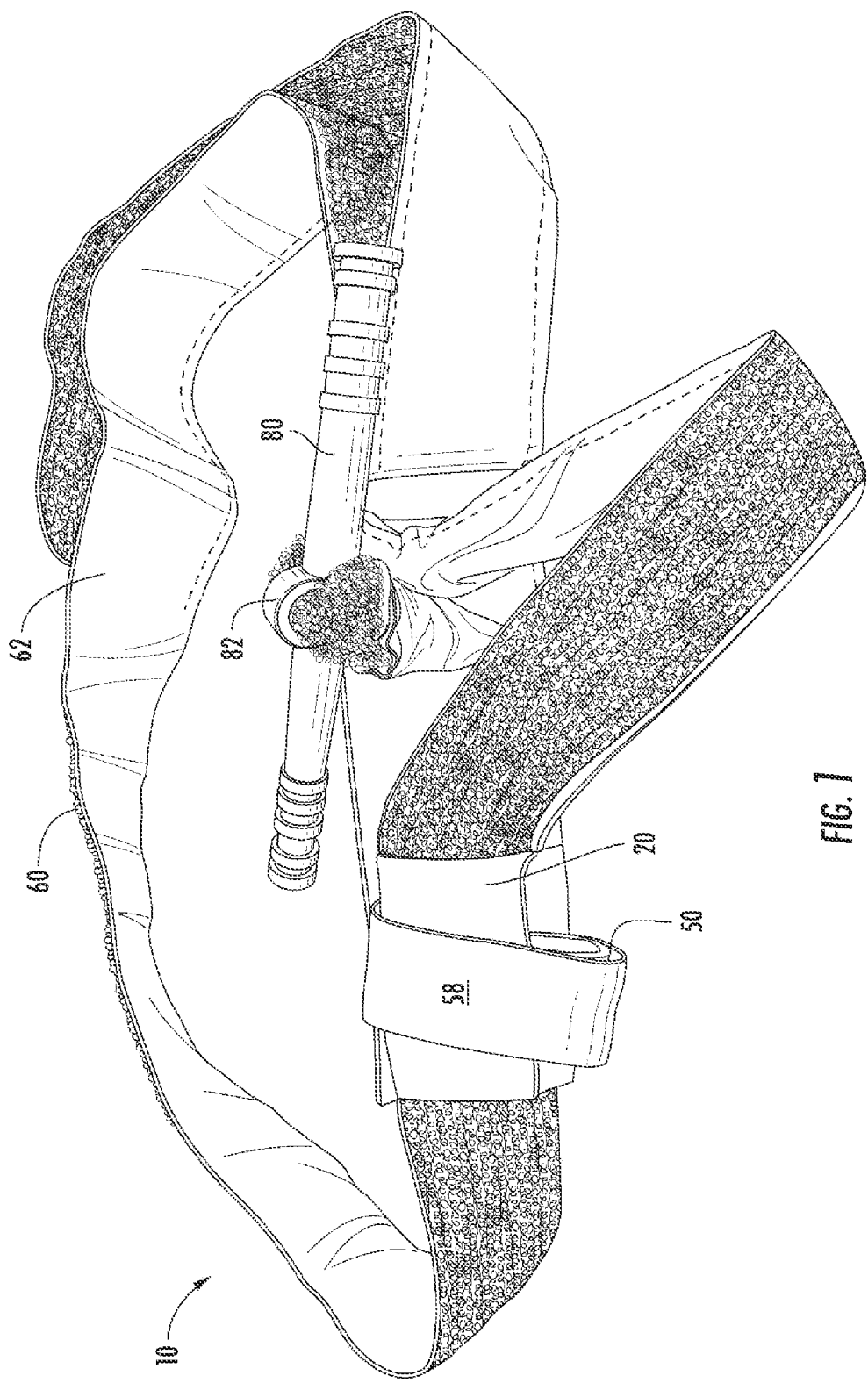
FIG. 1 is a perspective view of an embodiment of a tourniquet in accordance with the present disclosure.
Figure 2:
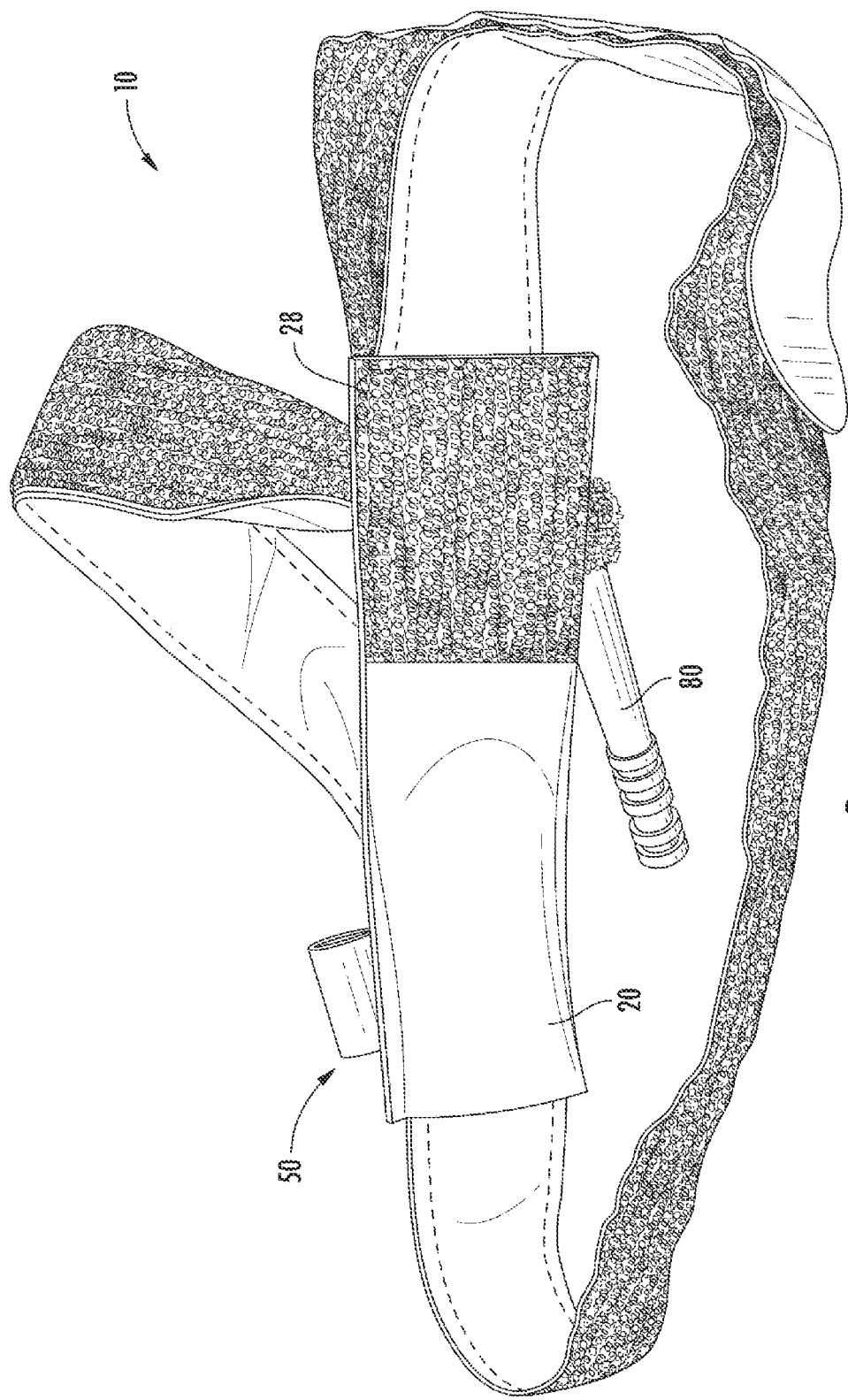
FIG. 2 is a perspective view of the tourniquet of FIG. 1 taken from a second view thereof.
Figure 3:
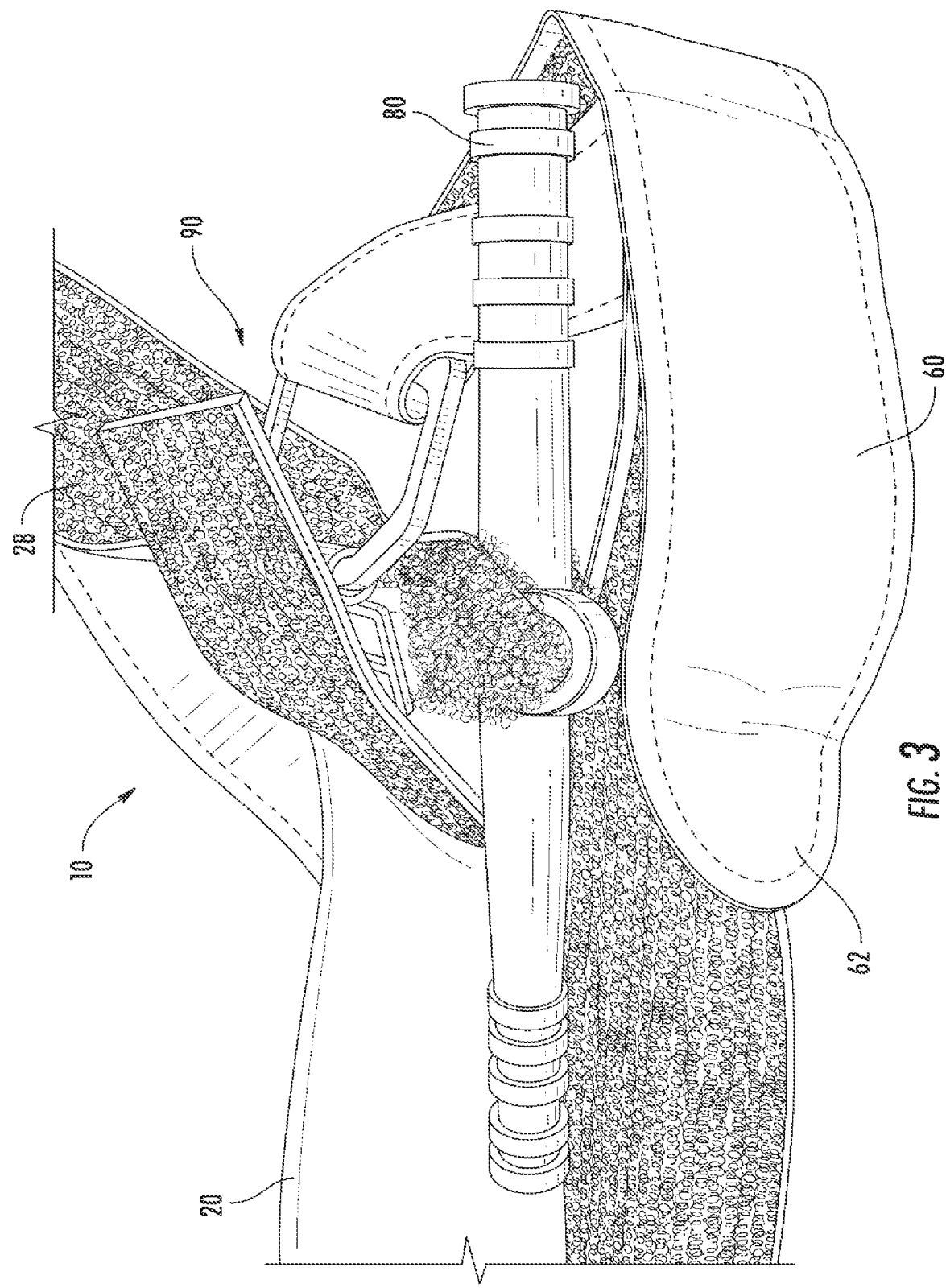
FIG. 3 is an enlarged perspective of a portion of the tourniquet of FIG. 1.
Figure 4:
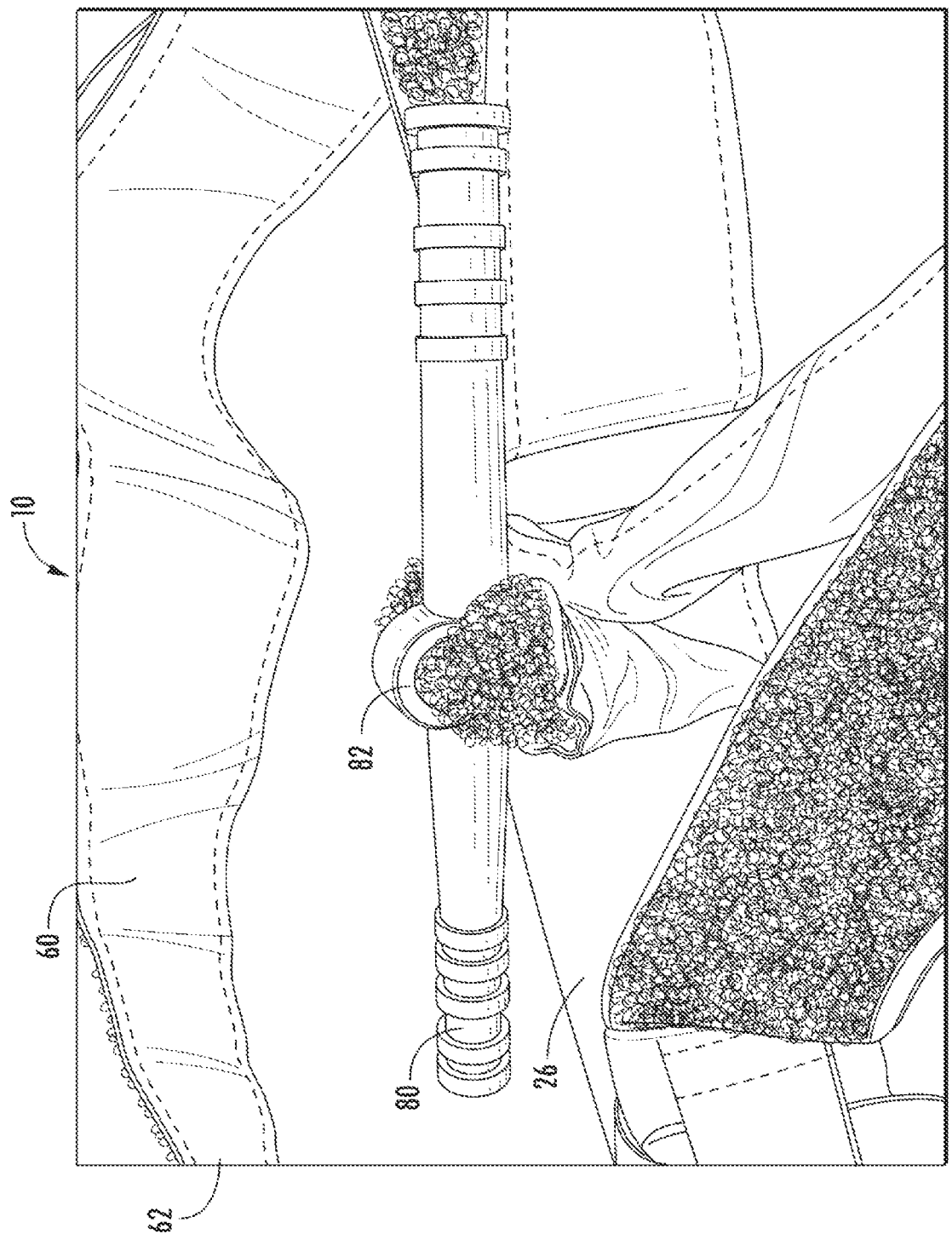
FIG. 4 is an enlarged perspective view of a portion of the tourniquet of FIG. 1 taken from another view.
Figure 7:
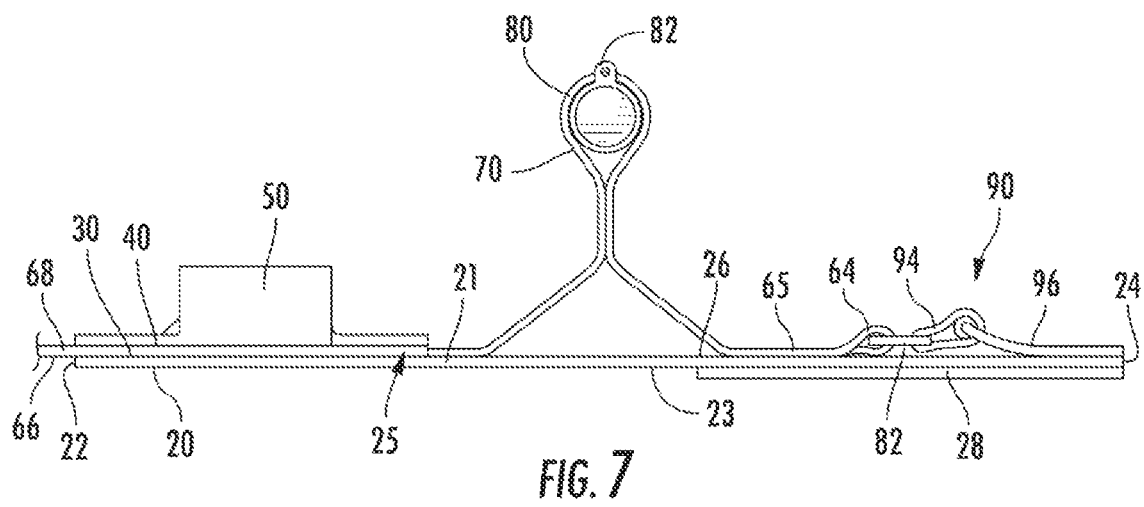
FIG. 7 is a side elevational view of the tourniquet portion of FIG. 5.
Figure 8:
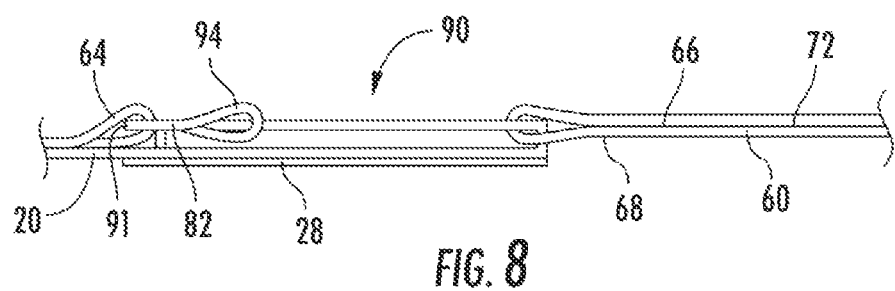
FIG. 8 is a side fragmentary view of the tourniquet of FIG. 1 with a compression strap thereof being secured in position under compression, portions of the strap being omitted.

The principal foundational structure of the tourniquet 10 is an elongated rectangular web 20 of woven nylon material which has a length of approximately 6¾ inches and a generally uniform width of 2 inches. For descriptive purposes, the web 20 extends from a rear end 22 to a frontal end 24 and has an upper (top) surface 21 and a lower (bottom) surface 23. An intermediate portion of the web 20 mounts a substantially square reinforcement pad 26 of woven nylon material which is glued or otherwise secured to the top of the web. A forward portion of the web includes a bottom pad 28 of soft felt-like surface composition which is stitched to the underside of the web (FIGS. 7, 8). The cushioned lower pad 28 is approximately 2 inches by 2¾ inches in one preferred embodiment.

The web 20 mounts an overlay strip 30 of woven nylon material which has a length of approximately 2¼ inches and a width of approximately 2 inches. The overlay 30 is stitched at opposing longitudinal sides to the web 20 to form a rear end 32 at the rear end 22 of the web and a frontal end 34. The interior surface of the overlay and the opposed web form a slide 25, as will be further described below. The web 20 functions as a flexible highly conforming support structure for the tourniquet so that upon application, the tourniquet more effectively conforms to a shape about the limb that is optimal for constriction purposes.

A strip 40 of nylon material is stitched to the upper surface of the overlay at opposed ends to capture a retainer 50. The retainer 50 is preferably formed of a rugged plastic material configured to form opposed C-shaped catches 52 and 54 (FIGS. 6, 9) connected by a crosspiece 53. The crosspiece 53 is captured in fixed position by strip 40. The catches have a maximum interior separation of approximately 2 inches and have longitudinal edges which are separated by approximately 1 inch and are dimensioned to receive and capture a windlass, as described below.

The exterior surface of the retainer 50 is affixed with a hook and loop fabric fastening material 56. A band 58, which is preferably white, is glued or otherwise secured to a portion of the underside of the retainer and is extendable around the upper and side portions of the retainer to provide a selectively positionable securement band across the gap between the edges of the catches 52 and 54. The securement band 58 has a bottom surface affixed with hook and loop material 59 removably engageable with the side hook and fabric material 56 to provide a secured fastening engagement. The removable position of the band is designated by 58' in FIG. 5. The upper portion of the band 58 preferably includes a TIME indicia on the white background so that the time of the application of pressure can be conspicuously recorded. The retainer 50 is secured to the overlay 30 via the strip 40 in a fashion so that the retainer essentially extends transversely and is relatively fixed to the overlay 30, as well as the web 20, to minimize twisting, contortion and/or rotation.

Figure 11:
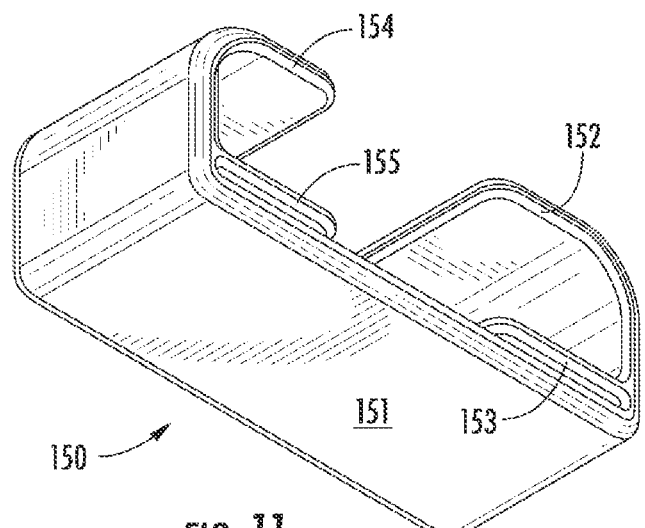
FIG. 11 is an enlarged perspective view of an alternative embodiment of a retainer which may be employed in the tourniquet.
Figure 12:
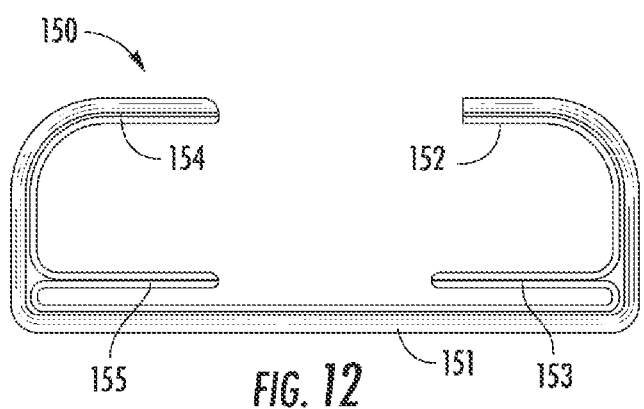
FIG. 12 is an end elevational view of the retainer of FIG. 11.
Figure 13:
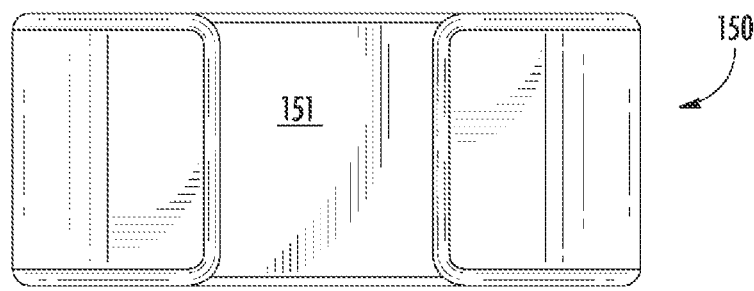
FIG. 13 is a top plan view of the retainer of FIG. 11.

With reference to FIGS. 11-13, an alternative embodiment of the retainer is generally designated by the numeral 150. The retainer 150 is formed of rugged plastic material and is configured to form opposed C-shaped catches 152 and 154. The catches have a maximum interior separation of approximately 2 inches and have longitudinal edges which are separated by approximately 0.75 inch-1 inch. The catches are dimensioned to receive and capture a windlass as described. The retainer 150 includes opposed inwardly projecting tabs 153 and 155 which are separated approximately 0.75 inch-1 inch and are spaced above the retainer bottom panel 151 by approximately 1/16 inch. These tabs capture the strip 40 of nylon material. In all other respects, the retainer 150 functions substantially the same way as the previously described retainer 50.

A compression assembly comprises a compression strap 60, a windlass 80 and a buckle assembly 90 to implement the compressive force applied by the tourniquet. The elongated compression strap 60 is approximately 4 feet in length in one embodiment. The compression strap 60 has a tapered insertion end 62 and a generally opposed mounting loop 64 wherein the strap is reversed and double stitched to the web 20 and through the pad 28 at a compound anchor position 65. The strap preferably has a double layer with a first (upper) layer 66 of woven nylon material and a second (lower) layer 68 of smooth nylon material stitched together along their longitudinal length. The strap 60 is configured to withstand substantial longitudinal stresses.

Figure 14:
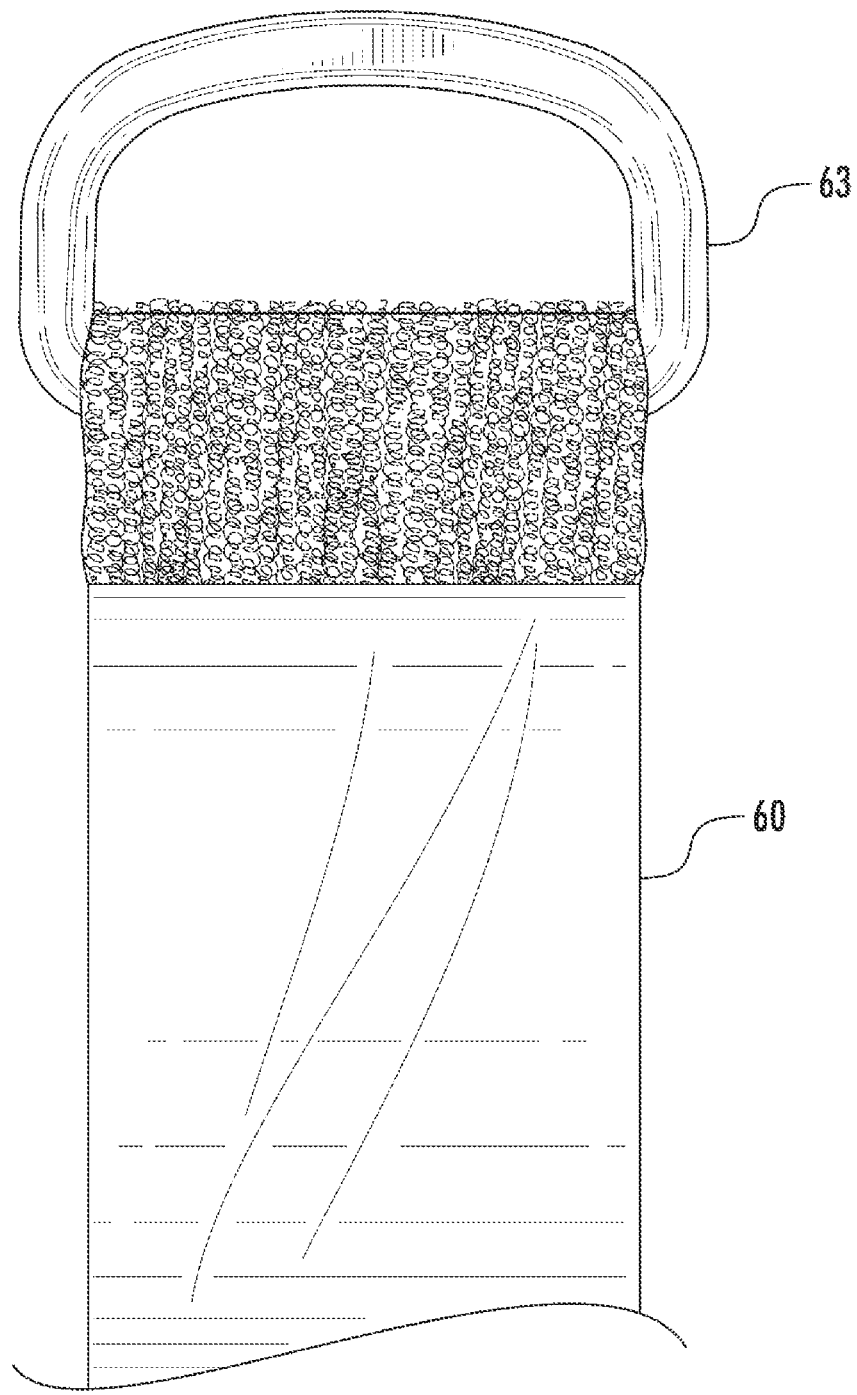
FIG. 14 is an enlarged fragmentary view of a compression strap and a D-ring employed in an alternative tourniquet embodiment.

With reference to FIG. 14, in some embodiments the compression strap 60 does not have a tapered end, but mounts an enlarged pull member, preferably in the form of a D-ring 63. In this embodiment, the strap 60 is pre-inserted through an opening in a second D-ring 96, as described below. The enlarged D-ring is dimensioned to prevent the strap from disengaging from D-ring 96 to prevent twisting when the strap is applied to the injured person. D-ring 63 also has a distinctive color, such as red, to facilitate the usage of the tourniquet.

The strap 60 extends from the anchor position 65 approximately 1 inch where it is connected in back-to-back relationship to form a closed loop-like windlass connector 70 (FIGS. 5, 7), as will be further described. The strap 60 then extends through the slide 25 and forwardly with the surface 68 being generally disposed to slide across an upper surface 21 of the web 20. The upper surface layer 66 of the strap includes an extensive hook-and-loop fabric connection 72 which functions as will be later described below. In one preferred embodiment, the connection 72 does not extend the entire length of surface layer 66, but terminates approximately 4 inches from the retainer 50. The connector 70 of the compression strap 60 is proximate the retainer 50 and intermediate the retainer 50 and the mounting loop 64 to form a quasi-V-shaped gap in an unactuated mode, as best illustrated in FIG. 7.

The windlass 80 is a sturdy, elongated quasi-rod-like member which has a length of approximately 6 inches and has an integral medial projecting eye 82. The eye 82 preferably forms a round opening. The eye receives the connector 70 of the strap to confine the windlass to a generally fixed longitudinal position on the strap. The round opening of the eye 82 of the windlass provides for a greater wall thickness and increases the strength and integrity of the windlass 80. This feature can be contrasted with a conventional tourniquet windlass having a medial slot which tends to result in thinner wall structures and thus less strength and potentially greater stress at the ends of the medial slot. In addition, the round opening in the eye 82 tends to force the connector 70 to curl up on its sides into a conformable round-type configuration upon winding or rotating the windlass in contrast to piling up flat or semi-flat layers of material when a slot-like configuration is employed. Consequently, the connector 70 and the eye 82 cooperate to provide a more effective tensioning upon rotating the windlass. The windlass 80 may have various configurations which facilitate manual gripping and, in one embodiment, is formed of heavy-duty plastic.

Figure 10A:
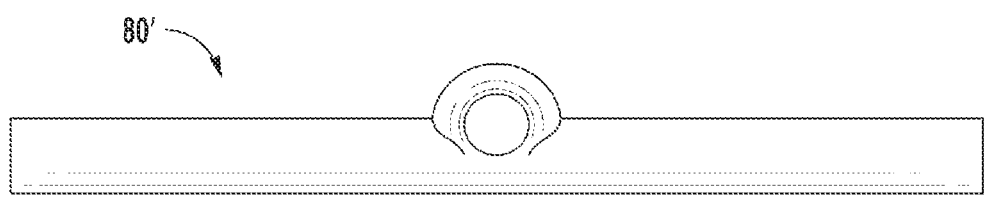
FIGS. 10A and 10B are enlarged side views of alternative embodiments of a windlass that are employed in the tourniquet of FIG. 1.
Figure 10B:
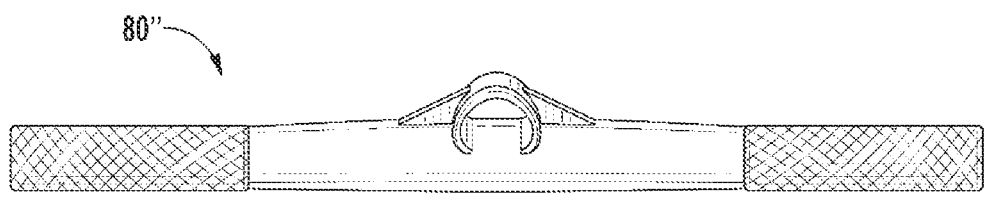

An alternative embodiment of a windlass is shown in FIG. 10A and designated by 80'. Another embodiment of a windlass is shown in FIG. 10B and designated by 80". Windlass 80" has knurled end portions to facilitate gripping and a slightly bulbous or enlarged diameter medial portion. The functional description of windlass 80 applies to windlass 80' and windlass 80".

Figure 9:
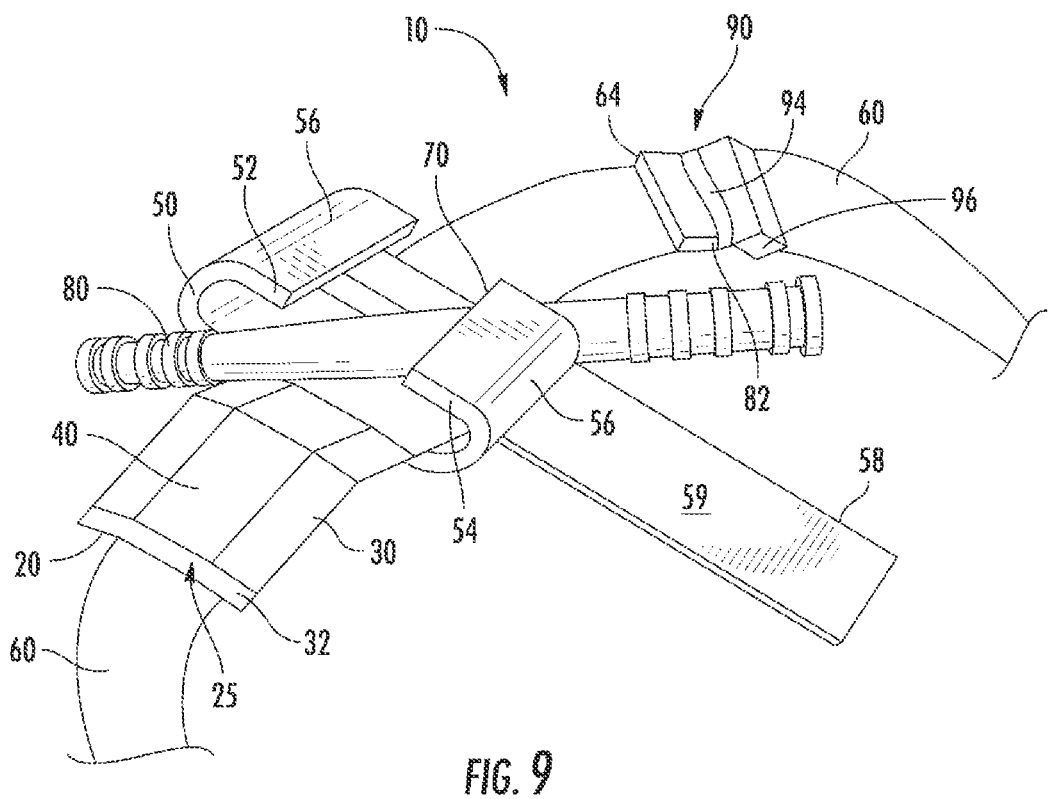
FIG. 9 is a perspective view of a portion of the tourniquet of FIG. 1 with tourniquet being tightened under compression and a windlass being engaged with a retainer prior to a retainer securing band being positioned and fastened in place.

Rotation of the windlass 80 causes the strap to wrap about the connector and draws the strap frontally through the slide 25 toward the connector thereby effectively tensioning the strap after it is wrapped around the limb, as described below. It will be appreciated that the windlass 80 is positioned so that upon rotation, one of the ends of the windlass can be received in or captured by the retainer and secured therewith by the band 58, as schematically shown in FIG. 9. Rotation of the windlass results in a counter-rotation force which urges the end of the windlass to engage the catches 52 and 54 which are generally fixed against counter-rotation.

With reference to FIG. 5, the buckle assembly 90 is a multi-component assemblage comprising a frame-like clip 82 having a pair of parallel bars 91 and 93. Bar 91 is retained in the loop-like connector 64. The second bar 93 mounts a clasp 94 which pivotally receives a central medial linear section 95 of a D-ring 96. The D-ring has a bar 98 which defines an opening for receiving the end 62 of the strap or through which the strap 60 extends if it has an enlarged D-ring 63 at its end to ensure extension through D-ring 96 at all times. The D-ring 96/D-ring 63 interaction also prevents twisting of the compression strap 60. The construction of the buckle assembly effectively reduces stress on the buckle assembly due to the extreme stress/pressure applied by the compression strap 60. The limited multi-pivotal configuration of the buckle assembly 90 allows for enhanced flexibility during application of the tourniquet and subsequent tightening. The parallel bars 91 and 93 of the clip and the ring bar 98 ensure that the strap will not twist and distort when the pressure is applied to the strap.

The tourniquet 10 is preferably pre-assembled so that the buckle assembly 90 is snapped together via the clasp 94 and the strap 60 is pre-fed through the D-ring 96. The buckle assembly 90 can be separated for easier tourniquet application if advantageous for the treatment of the patient and positively snapped together in instances where it is advantageous for the treatment of the patient.

The buckle assembly 90 does not incorporate teeth which can grip the strap 60 as it is being tightened, thereby compromising tension of the initial application and also thereby compromising the effectiveness of the windlass 80 if excessive turns are required to reach the desired tension. The toothless buckle assembly 90 thus allows a smooth application to ensure a large tension is achieved before rotating the windlass to achieve the final maximum tension applied to terminate bleeding from the wound.

In operation, the tourniquet 10 is wrapped around the limb (not illustrated) between the heart and the wound with the underside of the web 20 and the cushion pad 28 and the layer 68 of the strap 60 engaging against the limb. The end 62 of the strap is then pulled and inserted up through the D-ring 96 and pulled around bar 98 (or if the strap 60 is pre-inserted, the D-ring 63 is pulled) in a reverse fashion. The strap is pulled tight and the fastener portion 72 on the surface of the strap is then engaged along a substantial interface so that a secure tight fit of the strap about the limb is obtained.

The extensive hook and loop fabric connection 72 provides a large connection interface and support for securing the tourniquet at a maximum initial tensioning without the risk of slippage that could occur with teeth or other temporary fastening means. The connection 72 also facilitates an easier and more effective one-handed application in cases where the tourniquet is being self-applied. It should be appreciated that the smooth side 68 of the strap engages against a substantial circumference of the limb. Additional pressure is then applied by rotating the windlass 80 which causes the strap to tighten even more about the limb. When a sufficient pressure is obtained on the strap to terminate the bleeding, one end of the windlass 80 is then engaged in a catch 52 or 54 wherein the windlass is captured by the retainer. The band 58 is then applied and fastened over the retainer to secure the windlass (and the strap) in a secured position with the enhanced tourniquet pressure being maintained on the limb.

The occluding pressure on the wound can then be effectively and reliably maintained until appropriate medical assistance has been obtained.

The compression assembly comprising the strap 60, the windlass 80 and the buckle assembly 90 is cooperatively configured so that only a relatively small rotation of the windlass 80 is required to apply the final additional pressure.

While preferred embodiments of the foregoing have been set forth for purposes of illustration, the foregoing description should not be deemed a limitation of the invention herein. Accordingly, various modifications, adaptations and alternatives may occur to one skilled in the art without departing from the spirit and the scope of the present invention.

The invention claimed is:

1. A tourniquet comprising:
   a first member;
   a second member having first and second ends attached at opposite longitudinal sides to said first member to form a slide;
   a retainer having opposed catches mounted to said second member;
   an elongated third member having opposed first and second sides and forming a closed first loop and a closed second loop and secured to said first member at a location between said first and second loops;
   a windlass having an eye protruding from a medial portion and receiving a portion of said third member extending to form said closed second loop, said windlass being capturable in said retainer;
   a clip having a pair of first and second parallel bars, said first bar being pivotally retained by said first loop and said second bar mounting a clasp;
   a D-ring retained by said clasp;
   a hook and loop fabric connector disposed on the first side of said third member;
   wherein said third member is slidable in said slide between said first and second members and extendable through said D-ring and engageable about a limb and securable in a taut engagement by said hook and loop fabric connector;
   wherein said third member is further tightenable by rotating said windlass to an occluding position which is maintainable by securing said windlass in said retainer.

2. The tourniquet of claim 1 wherein said D-ring is dismountable from said clasp.

3. The tourniquet of claim 1 wherein said windlass has a quasi-rod-like shape with said eye protruding from the medial portion.

4. The tourniquet of claim 1 wherein said retainer comprises a plastic member having C-shaped catches.

5. The tourniquet of claim 4 further comprising a strip of material securing said retainer to said second member wherein said retainer further comprises a pair of transversely spaced tabs which engage said strip of material.

6. The tourniquet of claim 1 wherein said third member comprises two layers of elongated nylon material stitched longitudinally at opposed sides.

7. The tourniquet of claim 1 wherein a securement band is positionable over said catches and removably securable thereto.

8. The tourniquet of claim 1 further comprising a reinforcement pad attached to said first member.

9. The tourniquet of claim 1 further comprising a cushion pad attached to said first member.

10. A tourniquet comprising:
    a first member;
    a second member having first and second ends attached at opposite longitudinal sides to said first member;
    a retainer having opposed catches extending from a cross piece wherein a strip of material is mounted to said second member and said strip of material captures said cross piece;
    an elongated third member having opposed first and second sides and forming a closed first loop and a closed second loop and secured to said first member at a location between said first and second loops;
    a windlass having an eye protruding from a medial portion and receiving a portion of said third member, said windlass being capturable in said retainer;
    a first buckle member having a pair of first and second parallel bars, said first bar being pivotally retained by said first loop and said second bar mounting a clasp;
    a second buckle member retainably engageable by said clasp;
    a hook and loop fabric connector disposed on the first side of said third member;
    wherein said third member is slidable between said first and second members and extends through said second buckle member and is engageable about a limb and securable in a taut engagement by said hook and loop fabric connector;
    wherein said third member is further tightenable by rotating said windlass to an occluding position which is maintainable by securing said windlass in said retainer.

11. The tourniquet of claim 10 wherein said second buckle member is disengageable from said clasp.

12. The tourniquet of claim 10 wherein said windlass has opposed end portions having a quasi-rod-like shape.

13. The tourniquet of claim 10 wherein said retainer is a plastic component.

14. The tourniquet of claim 10 wherein said third member comprises two layers of elongated nylon material stitched together.

15. A tourniquet comprising:
    a first member;
    a second member having first and second ends attached at opposite longitudinal sides to said first member;
    a retainer having opposed C-shaped catches and a cross piece and wherein a strip of material is mounted to said second member and said strip of material captures said cross piece;
    an elongated third member having opposed first and second sides and forming a closed first loop and a closed second loop and secured to said first member;
    a windlass having an eye protruding from a medial portion and receiving a portion of said third member extending to form said closed second loop, said windlass being capturable in said retainer;
    a first buckle member having a pair of first and second parallel bars, the first bar being pivotally retained by said first loop and said second bar mounting a clasp;
    a second buckle member retainably engageable by said clasp;
    a connector disposed on the first side of said third member;
    wherein said third member is slidable between said first and second members and extends through said second buckle member and is engageable about a limb and securable in a taut engagement by said connector;
    wherein said third member is further tightenable by rotating said windlass to an occluding position which is maintainable by securing said windlass in said retainer.

16. The tourniquet of claim 15 wherein said second buckle member is a D-ring.

17. The tourniquet of claim 15 wherein said connector is a hook and loop fabric connector.

18. The tourniquet of claim 17 wherein said retainer is a plastic component and a securement band is mounted to said plastic component and said securement band is removably securable to said retainer to secure said windlass in said retainer.

19. The tourniquet of claim 18 wherein said securement band is secured by a hook and loop fabric connector.

20. The tourniquet of claim 15 wherein said windlass is a plastic component having a quasi-rod-like shape, the medial portion is enlarged and the eye protrudes integrally from the enlarged medial portion.

\* \* \* \* \*